(12) United States Patent
Soin

(10) Patent No.: US 11,752,143 B2
(45) Date of Patent: *Sep. 12, 2023

(54) METHODS OF USING LOW DOSE NALTREXONE TO TREAT CHRONIC PAIN

(71) Applicant: Amol N. Soin, Dayton, OH (US)

(72) Inventor: Amol N. Soin, Dayton, OH (US)

(73) Assignee: Soin Therapeutics LLC, Dayton, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/527,336

(22) Filed: Nov. 16, 2021

(65) Prior Publication Data

US 2022/0202807 A1 Jun. 30, 2022

Related U.S. Application Data

(60) Provisional application No. 63/132,628, filed on Dec. 31, 2020.

(51) Int. Cl.
 *A61K 31/485* (2006.01)
 *A61K 9/20* (2006.01)
 *A61P 25/04* (2006.01)

(52) U.S. Cl.
 CPC .......... *A61K 31/485* (2013.01); *A61K 9/2072* (2013.01); *A61P 25/04* (2018.01)

(58) Field of Classification Search
 CPC ......... A61K 31/485; A61P 25/04; A61P 29/00
 USPC ...................................................... 514/282
 See application file for complete search history.

(56) References Cited

U.S. PATENT DOCUMENTS

| | | |
|---|---|---|
| 8,912,211 B2 | 12/2014 | Chapleo |
| 10,111,870 B2 | 10/2018 | Griffin |
| 2005/0038062 A1 | 2/2005 | Burns |
| 2007/0259939 A1 | 11/2007 | Stebbing |
| 2009/0143367 A1 | 6/2009 | Malamas |
| 2009/0270400 A1 | 10/2009 | Auguet |
| 2013/0059876 A1 | 3/2013 | Angeli |
| 2014/0155424 A1 | 6/2014 | Ehrich |
| 2014/0356341 A1 | 12/2014 | Felder |
| 2015/0111916 A9 | 4/2015 | Toledano |
| 2017/0014404 A1 | 1/2017 | McKinney |
| 2017/0020862 A1 | 1/2017 | Brown |
| 2017/0065579 A1 * | 3/2017 | Voigt et al. .......... A61K 31/485 514/282 |

OTHER PUBLICATIONS

Zappaterrra, M. et al.: Low-dose naltrexone reduces symptoms in stiff-person syndrome. Medical Hypotheses, vol. 137, p. 109546, 2020.*
Metyas, S. et al.: Low dose naltrexone in the tratment of Fibromyalgia. Corrent Rheumat. Rev., vol. 14, pp. 177-180, 2018.*
https://www.mipmpc.com/pain-management/low-dose-naltrexone-and-pain/; "Low Dose Naltrexone and Pain" Webpage Article at Huraibi Rehab Institute, PLLC; Dr. Pradeep Chopra; Oct. 27, 2021.
http://www.lowdosenaltrexone.org; "Low Dose Naltrexone" Website; Received Jan. 18, 2019.
https://www.ldnscience.org/; LDN Science Website; LDNscience® Public Information Project of the MedInsight® Research Institute; Received Nov. 16, 2021.
https://www.ncbi.nlm.nih.gov/pmc/articles/PMC3661907/pdf/11481_2013_Article_9451.pdf; "Treatment of Complex Regional Pain Syndrome (CRPS) Using Low Dose Naltrexone (LDN)"; Pradeep Chopra; Apr. 2, 2013.
https://med.stanford.edu/pain/snapl/current-studies/crps.html; "CRPS Treatment Study" Webpage from Stanford School of Medicine, Systems Neuroscience and Pain Lab; Received Nov. 16, 2021.
https://ldnresearchtrust.org/; LDN Research Trust Website; Received Nov. 16, 2021.

* cited by examiner

*Primary Examiner* — Charanjit Aulakh
(74) *Attorney, Agent, or Firm* — Neustel Law Offices

(57) ABSTRACT

Methods of using low dose naltrexone to treat chronic pain in a patient. The methods of using low dose naltrexone to treat chronic pain generally includes administering to the patient a first amount of naltrexone in an immediate-release agent and a second amount of naltrexone in a modified-release agent.

20 Claims, No Drawings

METHODS OF USING LOW DOSE NALTREXONE TO TREAT CHRONIC PAIN

CROSS REFERENCE TO RELATED APPLICATIONS

I hereby claim benefit under Title 35, United States Code, Section 119(e) of U.S. provisional patent application Ser. No. 63/132,628 filed Dec. 31, 2020. The 63/132,628 application is currently pending. The 63/132,628 application is hereby incorporated by reference into this application.

STATEMENT REGARDING FEDERALLY SPONSORED RESEARCH OR DEVELOPMENT

Not applicable to this application.

BACKGROUND

The described example embodiments in general relate to various methods of using low dose naltrexone to treat chronic pain in a patient.

Complex regional pain syndrome (CRPS) is a chronic neurological condition that can cause severe pain. CRPS is a rare, orphan chronic pain disorder affecting fewer than 200,000 individuals each year and is a rare or orphan disease. The characteristic feature of CRPS is hypersensitivity to stimulus resulting in pain, including allodynia, pain due to a stimulus that does not usually provoke pain, and hyperalgesia, increased pain from a stimulus that usually provokes pain. CRPS is a neuroinflammatory condition and patients frequently experience autonomic, sensory, vasomotor, and motor dysfunction (such as pain in their limbs and dystonia).

CRPS is divided into two categories. CRPS Type 1 (also known as reflex sympathetic dystrophy or RSD) occurs in the absence of confirmed nerve injury. CRPS Type 2 (previously known as causalgia) occurs with confirmed nerve injury.

The cause of CRPS is likely multifactorial and the exact mechanism is still unclear. However, evidence suggests that Toll-like receptors (TLR4) and inflammatory cytokines play key roles in the mechanistic pathway. The TLR4 receptor is believed to be upregulated during neuroimmune activation, which triggers the production of proinflammatory cytokines, leading to allodynia and hyperalgesia.

Because of the rarity of CRPS, little high-quality research has been performed to evaluate optimal management strategies. Currently, there is no FDA approved treatment for CRPS and it is an unmet medical need. Current treatment of CRPS includes physical and occupational therapy, pharmacotherapies, and interventional procedures. Pharmacologic treatments focus on traditional medicines for pain management, including steroids and opioids. Much of the current research is inconclusive as to the efficacy of opioid treatment for CRPS.

SUMMARY

One example embodiment is directed to various methods of using low dose naltrexone to treat chronic pain in a patient. The methods of using low dose naltrexone to treat chronic pain includes administering to the patient a first amount of naltrexone in an immediate-release agent and a second amount of naltrexone in a modified-release agent.

There has thus been outlined, rather broadly, some of the embodiments of the present disclosure in order that the detailed description thereof may be better understood, and in order that the present contribution to the art may be better appreciated. There are additional embodiments that will be described hereinafter and that will form the subject matter of the claims appended hereto. In this respect, before explaining at least one embodiment in detail, it is to be understood that the various embodiments are not limited in its application to the details of construction or to the arrangements of the components set forth in the following description or illustrated in the drawings. Also, it is to be understood that the phraseology and terminology employed herein are for the purpose of the description and should not be regarded as limiting.

To better understand the nature and advantages of the present disclosure, reference should be made to the following description and the accompanying figures. It is to be understood, however, that each of the figures is provided for the purpose of illustration only and is not intended as a definition of the limits of the scope of the present disclosure. Also, as a general rule, and unless it is evidence to the contrary from the description, where elements in different figures use identical reference numbers, the elements are generally either identical or at least similar in function or purpose.

BRIEF DESCRIPTION OF THE DRAWINGS

No figures are included with this application.

DETAILED DESCRIPTION

A. Overview

1. Naltrexone

Naltrexone is approved for use in the treatment of alcohol use disorders (AUD) and other addictions, such as opioid dependence, e.g., a daily 50 mg tablet or weekly 380 mg extended-release suspension. At standard dosage, naltrexone functions as an opioid antagonist having a competitive binding affinity for μ-opioid receptors. As used herein, naltrexone includes (but is not limited to) naltrexone, its metabolites, including 6β-Naltrexol, enantiomers, including (+)-naloxone, isomers and racemic mixtures of same, in both free base and salt forms.

The disease state of CRPS involves inflammatory cytokines that circulate along the patient's body. These inflammatory cytokines are known to cause some of the specific symptoms that result from CRPS including edema, swelling, hypersensitivity to touch, allodynia, vasomotor and pseudo motor changes, and regulation of the inflammatory cytokine release.

Low-dose naltrexone is believed to down-regulate inflammatory cytokine release, which is important in patients who have complex regional pain syndrome (CRPS). Low-dose naltrexone's affect on cytokine release, in particular, is beneficial to CRPS.

From a mechanistic standpoint, naltrexone is an antagonist to opioid receptors and has the highest affinity to the mu-opioid receptor and, it is an antagonist of Toll-like receptors (TLR). TLRs lead to production of pro-inflammatory cytokines when they are activated, so antagonizing TLRs decreases the activation of pro-inflammatory cytokines. Pro-inflammatory cytokines increase inflammation, and this is a hallmark of the disease of CRPS because you see inflammation, hypersensitivity to touch, and allodynia which all occur as a result of CRPS. So by blocking this, we are actually treating what likely is the mechanism of action specific to this particular disease state. This is counterintuitive as Naltrexone typically antagonizes opioids which are typically used to treat pain.

Naltrexone in higher doses functions as an opioid antagonist targeting the mu and delta opioid receptors. Off-label uses of naltrexone have explored its use at lower doses through a different mechanism for the treatment of inflammatory, rheumatological, and neurological conditions. These conditions include multiple sclerosis, fibromyalgia, Crohn's disease, chronic fatigue syndrome (CFS), and—more recently—CRPS. At the low doses used for these conditions, naltrexone is thought to act as an immune modulator. Some speculate that this mechanism is caused by reduced neuroinflammation in the case of disorders like CFS. Evidence suggests that, at low doses, naltrexone antagonizes TLR4 on activated glial cells without the previously mentioned function as a mu opioid receptor antagonist. Thus, low-dose naltrexone presents a promising therapeutic avenue for the treatment of CRPS, a condition in which TLR4 upregulation is a primary pathway through attenuation of glial cell activation and direct targeting of TLR4 activity.

In contrast with standard-dose naltrexone (i.e. 50 mg or higher), low-dose naltrexone is believed to exert its mechanism of action through interaction with and antagonism of Toll-like receptor 4 (TLR4). TLR4 has been shown to be a key mediator of microglial cell activation, which has been identified as a causal mechanism of neuropathic pain in CRPS. Microglial cell activation is associated with the release of pro-inflammatory cytokines, reactive oxygen species, and prostaglandins, which amplify the inflammatory response. Another potential mechanism of action of low-dose naltrexone treatment is a paradoxical upregulation of opioid signaling. Low-dose naltrexone leads to transient opioid receptor blockade, which triggers a positive feedback mechanism that increases the production of endogenous opioids (endogenous endorphins and enkephalins) and opioid signaling. Together, these mechanisms may work to alleviate pain associated with CRPS.

Not only does low-dose naltrexone treat the pain symptom of CRPS, but it can also treat the disease process and disease cascades, since patients who suffer from CRPS have not only increased neuro-inflammation and inflammatory cytokines, but also a decrease in endorphin and enkephalin circulation compared to the average patient. Increasing endogenous enkephalins and endorphins would help from a symptomatic standpoint. Blocking the Toll-like receptors would help the entire cascade of the disease, decreasing the production of pro-inflammatory cytokines, and attenuation of the microglia and glial cells in the central and peripheral nervous system. It may actually treat the underlying disease state, which would be extremely beneficial to the patient.

2. Central Nervous System

Glial cell activation, inflammatory cytokines, and neuro-inflammation are hallmarks of the disease of CRPS. The toll-like receptor activity is very important when looking at complex regional pain syndrome specifically.

In the central nervous system, low-dose naltrexone reduces toll-like TOR signaling in glial cell activation. Naltrexone is an antagonist of TOR. TOR activation leads to the production of NF-KB, which is an inflammatory signaling pathway. NF-KB is a tumor growth factor, but this is also important in the inflammatory signaling pathway. This results primarily in a reduction of inflammatory cytokines, but also reduces neuro-inflammation. This mechanism of action of low-dose naltrexone is particularly important in patients experiencing CRPS. CRPS patients suffer from severe debilitating pain, with even light touch or benign stimulation eliciting extreme amounts of pain. Microglial cells and glial cells are oftentimes involved in this pain-signaling pathway, and reduction in glial cell activation can help treat this pain syndrome.

3. Peripheral Nervous System

Low-dose naltrexone also has effects in the peripheral nervous system where low-dose naltrexone can modulate T and B lymphocyte production. In the periphery nervous system, low-dose naltrexone can also reduce interleukin 6, interleukin 12, and tumor necrosis factor alpha. This is very important in patients who suffer from CRPS, specifically. Patients who have CRPS often have an increase in inflammatory cytokines and may often note an increase in interleukin 6, interleukin 12, and tumor necrosis factor alpha. By reducing these inflammatory cytokines back to what would be a more normal state, it is likely that we would be able to treat the actual disease state of complex regional pain syndrome.

4. Endogenous Enkephalins and Endorphins

Another important part of low-dose naltrexone is that it increases endogenous enkephalins and endorphins which are the body's natural pain killers. For example, it is also noted that when taken at bedtime, the short-acting low-dose naltrexone binds to receptors, leading to a brief blockade of opioid receptors between 2:00 a.m. and 4:00 a.m. This blockade is believed to up-regulate vital life elements of the body and cause an increase in endorphin and enkephalin production. This increase in endorphins and enkephalins causes a decrease in patient pain.

B. First Amount of Naltrexone

The first amount of naltrexone is administered to the patient directly or within an immediate-release agent in a manner allowing for uptake of the first amount of naltrexone by the patient within a short period of time (e.g. less than two hours in one example embodiment; less than 30 minutes in another example embodiment). The first amount of naltrexone may be selected based on the weight, sex or age of a given patient or various other factors. Various types of immediate-release agents may be used to administer the first amount of naltrexone.

In one example embodiment, the first amount of naltrexone ranges between approximately 1.5 mg to 5 mg. In another example embodiment, the first amount of naltrexone ranges between approximately 0.25 mg to 5 mg. In another example embodiment, the first amount of naltrexone ranges between approximately 0.25 mg to 2.00 mg. In another example embodiment, the first amount of naltrexone is approximately 1.5 mg. In another example embodiment, the first amount of naltrexone is approximately 1.0 mg. In another example embodiment, the first amount of naltrexone is approximately 2 mg.

C. Second Amount of Naltrexone

The second amount of naltrexone is administered to the patient within a modified-release agent to allow uptake of the second amount of naltrexone to the patient over an extended period of time (e.g. in one example embodiment the extended period of time is two or more hours; in another example embodiment the extended period of time is greater than 30 minutes; in another example embodiment the extended period of time is between 30 minutes to two hours). In one example embodiment, the second amount of naltrexone is administered to the patient after the first amount of naltrexone has been administered to the patient. In another example embodiment, the second amount of naltrexone is administered to the patient while at least a portion of the first amount of naltrexone is being administered to the patient. The second amount of naltrexone may be selected based on the weight, sex or age of a given patient or various other factors.

In one example embodiment, the modified-release agent releases the second amount of naltrexone over a 30 minute to 24 hour period of time. In one example embodiment, the modified-release agent releases the second amount of naltrexone over a 30 minute to 4 hour period of time. In another example embodiment, the modified-release agent releases the second amount of naltrexone over a 30 minute to 1 hour period of time. In another example embodiment, the modified-release agent releases the second amount of naltrexone over a 30 minute to 3 hour period of time.

In one example embodiment, the second amount of naltrexone ranges between approximately 1.5 mg to 5 mg. In another example embodiment, the second amount of naltrexone ranges between approximately 1 mg to 5 mg. In another example embodiment, the second amount of naltrexone ranges between approximately 0.25 mg to 5 mg. In another example embodiment, the second amount of naltrexone is approximately 1.5 mg. In another example embodiment, the second amount of naltrexone is approximately 1.0 mg. In another example embodiment, the second amount of naltrexone is approximately 2 mg.

In one embodiment, the modified-release agent is comprised of a slow-release agent. In another embodiment, the modified-release agent is comprised of a controlled release agent. In another embodiment, the modified-release agent is comprised of a sustained release agent. Various types of modified-release agents may be used to administer the second amount of naltrexone.

D. Combined Total Amount of Naltrexone

In one example embodiment, the first amount of naltrexone and the second amount of naltrexone combined equal a total amount of naltrexone that is a low-dosage of naltrexone. In another example embodiment, the first amount of naltrexone and the second amount of naltrexone combined equal a total amount of naltrexone that does not exceed 10 mg daily for a patient. In another example embodiment, the first amount of naltrexone and the second amount of naltrexone combined equal a total amount of naltrexone that does not exceed 5 mg daily for a patient. In another example embodiment, the total amount of naltrexone administered to the patient daily ranges between approximately 1 mg to 5 mg. In another example embodiment, the total amount of naltrexone administered to the patient daily is approximately 4.5 mg. In another example embodiment, the total amount of naltrexone administered to the patient daily is approximately 2 mg.

In another example embodiment, the total amount of naltrexone administered to the patient is approximately 2 mg per day for approximately 4 weeks followed by 4 mg per day after the initial 4 weeks to treat the chronic pain disorder (e.g. CRPS). It can be appreciated that the initial period of time for treating the patient may exceed or be less than 4 weeks.

In another example embodiment, the total amount of naltrexone administered to the patient is approximately 2 mg per day for approximately 4 weeks followed by 4 mg per day after the initial 4 weeks to treat the chronic pain disorder (e.g. CRPS).

E. Methods and Systems of Administration to Patient

The first amount of naltrexone in the immediate-release agent and the second amount of naltrexone in a modified-release agent may be administered to a patient in one of various methods such as orally (e.g. pill, liquid, suspension), transdermally (e.g. transdermal patch), topically, via injection, e.g., intravenous or intramuscular, inhalation, rectally, or the like.

In one example embodiment, the first amount of naltrexone and the second amount of naltrexone are administered simultaneously via a pill ingested by the patient. In another example embodiment, the first amount of naltrexone and the second amount of naltrexone are administered via a biphasic pill ingested by the patient. In one example embodiment of the naltrexone delivered via a pill, the pill is comprised of a bilayer pill with a first layer for the first amount of naltrexone and a second layer for the second amount of naltrexone. In another example embodiment of the naltrexone delivered via a pill, the pill is comprised of an inner portion with the second amount of naltrexone within the modified-release agent surrounded by an outer layer with the first amount of naltrexone within the immediate-release agent. One benefit of using a bilayer pill to administer the first amount of naltrexone and the second amount of naltrexone independently is the reduction of lucid dreaming and other side effects that can accompany high dosages of naltrexone.

F. Timing of Administration to Patient

In one example embodiment, the first amount of naltrexone in the immediate-release agent and the second amount of naltrexone in a modified-release agent may be administered simultaneously to the patient (e.g. via a pill, liquid solution). In another example, embodiment, the first amount of naltrexone in the immediate-release agent and the second amount of naltrexone in a modified-release agent may be administered to the patient at separate times with the second amount of naltrexone administered shortly after the first amount of naltrexone is administered to the patient.

In another example embodiment, the first amount of naltrexone and the second amount of naltrexone are administered to the patient in accordance with the patient's sleep cycle. In on such embodiment, the first and second amounts of naltrexone are administered approximately 30 minutes to 3 hours prior to the patient going to sleep. In another example embodiment, the first amount of naltrexone and the second amount of naltrexone are administered to the patient just prior to the patient going to sleep. One believed benefit of administering the low-dosage naltrexone within a few hours before the patient goes to sleep is because naltrexone works in part by stimulating endogenous endorphins (the body's natural pain killers) which are only produced by body in significant quantities beginning approximately 3-4 hours into the sleep cycle.

In another example embodiment, the first amount of naltrexone and the second amount of naltrexone are administered to the patient in a manner that maintains a concentration of naltrexone in the patient's circulatory system within an effective range over a twenty four hour period.

In one embodiment, a biphasic pill system is used to administer the naltrexone to the patient with a lower dosage of naltrexone for a first period of time followed by an increased dosage of naltrexone after the first period of time. In another example embodiment, a first total amount of naltrexone is administered to the patient daily for a first period of time and after the first period of time a second total amount of naltrexone is administered to the patient daily on a continuous basis to treat the chronic pain condition. In this example, the second total amount of naltrexone is higher than the first total amount of naltrexone. In one variation of this example, the second total amount of naltrexone is higher than the first total amount of naltrexone by at least two times. In another variation of this example, the first total amount of naltrexone is substantially equal to the second total amount of naltrexone.

G. Example Embodiments

1. First Example Embodiment

One example method of using low-dose naltrexone to treat chronic pain disorders generally comprises administering to the patient a first amount of naltrexone in an immediate-release agent and a second amount of naltrexone in a modified-release agent. Examples of chronic pain disorders include, but are not limited to, complex regional pain syndrome (CRPS), fibromyalgia, or neuropathic pain.

2. Second Example Embodiment

In a preferred example embodiment, a first total amount of naltrexone is administered to the patient daily for an initial period of time (e.g. approximately 4 weeks) followed by a second total amount of naltrexone per day after the initial period of time to treat the chronic pain disorder wherein the second total amount of naltrexone is higher than the first total amount of naltrexone. In the preferred embodiment, the naltrexone may be administered to a patient in one of various methods such as orally (e.g. pill, multilayered pill, liquid, suspension), transdermally (e.g. transdermal patch), topically, via injection, e.g., intravenous or intramuscular, inhalation, rectally, or the like.

In a variation of this preferred embodiment, the first total amount of naltrexone administered to the patient daily is comprised of the first amount of naltrexone at approximately 1 mg and the second amount of naltrexone at approximately 1 mg for the initial period of time (e.g. approximately 4 weeks), and then the second total amount of naltrexone administered to the patient daily after the initial period of time is comprised of the first amount of naltrexone at approximately 2 mg and the second amount of naltrexone at approximately 2 mg to treat the chronic pain disorder.

In another variation of this preferred embodiment, the first total amount of naltrexone administered to the patient daily in a multilayered pill is comprised of the first amount of naltrexone at approximately 1 mg in an immediate-release agent and the second amount of naltrexone at approximately 1 mg in a modified-release agent for the initial period of time (e.g. approximately 4 weeks), and then the second total amount of naltrexone administered to the patient daily after the initial period of time is comprised of the first amount of naltrexone at approximately 2 mg in an immediate-release agent and the second amount of naltrexone at approximately 2 mg in a modified-release agent to treat the chronic pain disorder.

In this variation of this preferred embodiment, the first total amount of naltrexone of approximately 2 mg is administered daily to the patient daily for the initial time period (e.g. 4 weeks) via a multilayered pill having an inner portion (or inner layer) with the second amount of naltrexone of approximately 1 mg within the modified-release agent surrounded by an outer layer with the first amount of naltrexone of approximately 1 mg within the immediate-release agent. In furtherance of this variation of the preferred embodiment, the second total amount of naltrexone of approximately 4 mg is administered daily to the patient daily after initial time period (e.g. after 4 weeks) via two multilayered pills each having an inner portion (or inner layer) with the second amount of naltrexone of approximately 1 mg within the modified-release agent surrounded by an outer layer with the first amount of naltrexone of approximately 1 mg within the immediate-release agent. The modified-release agent may be a controlled release agent, a sustained release agent or a slow-release agent.

3. Third Example Embodiment

In another preferred example embodiment, a method is disclosed of administering daily to the patient a first total amount of naltrexone for an initial period of time, wherein the first total amount of naltrexone is less than 3 mg. In furtherance of this preferred embodiment, the method is disclosed of administering daily to the patient a second total amount of naltrexone after the initial period of time, wherein the second total amount of naltrexone is less than 5 mg, and wherein the second total amount of naltrexone is greater than the first total amount of naltrexone. In one variation of this preferred embodiment, the second total amount of naltrexone is approximately two times greater than the first total amount of naltrexone. In another variation of this preferred embodiment, the first total amount of naltrexone is comprised of a first amount of naltrexone in an immediate-release agent and a second amount of naltrexone in a modified-release agent, and wherein the second total amount of naltrexone is comprised of a third amount of naltrexone in an immediate-release agent and a fourth amount of naltrexone in a modified-release agent. In another variation of this preferred embodiment, the first amount of naltrexone is approximately 1 mg, wherein the second amount of naltrexone is approximately 1 mg, wherein the third amount of naltrexone is approximately 2 mg, and wherein the fourth amount of naltrexone is approximately 2 mg. In another variation of this preferred embodiment, the first amount of naltrexone and the second amount of naltrexone are administered via a first pill ingested by the patient, wherein the first pill is comprised an inner layer with the second amount of naltrexone and an outer layer with the first amount of naltrexone, the third amount of naltrexone and the fourth amount of naltrexone are administered via a second pill ingested by the patient, wherein the second pill is comprised an inner layer with the fourth amount of naltrexone and an outer layer with the second amount of naltrexone.

4. Fourth Example Embodiment

In another preferred example embodiment of the method for treating a chronic pain disorder in a patient, the method comprises administering daily to the patient a first pill having a first total amount of naltrexone for an initial period (e.g. approximately four weeks), wherein the first total amount of naltrexone is comprised of a first amount of naltrexone in an immediate-release agent and a second amount of naltrexone in a modified-release agent, wherein the first amount of naltrexone is approximately 1 mg, wherein the second amount of naltrexone is approximately 1 mg, wherein the first amount of naltrexone and the second amount of naltrexone are administered via a first pill ingested by the patient, and wherein the first pill is comprised an inner layer with the second amount of naltrexone and an outer layer with the first amount of naltrexone. In furtherance of this preferred embodiment, the method further comprises administering daily to the patient a second pill having a second total amount of naltrexone after the initial period of time, wherein the second total amount of naltrexone is comprised of a third amount of naltrexone in an immediate-release agent and a fourth amount of naltrexone in a modified-release agent, wherein the third amount of naltrexone is approximately 2 mg, wherein the fourth amount of naltrexone is approximately 2 mg, wherein the third amount of naltrexone and the fourth amount of naltrexone are administered via at least one second pill ingested by the patient, wherein the at least one second pill is comprised an inner layer with the fourth amount of naltrexone and an outer layer with the third amount of naltrexone. One variation of this preferred embodiment includes where the second total amount of naltrexone is administered to the patient via two pills ingested by the pill, wherein each of the two pills are comprised of half the fourth amount of naltrexone (e.g. approximately 1 mg) in the modified-release agent in an inner layer and half the third amount of naltrexone (e.g. approximately 1 mg) in the immediate-release agent of an outer layer surrounding the inner layer.

Unless otherwise defined, all technical and scientific terms used herein have the same meaning as commonly understood by one of ordinary skill in the art to which this invention belongs. Although methods and materials similar to or equivalent to those described herein can be used in the practice or testing of the various embodiments of the present disclosure, suitable methods and materials are described above. All patent applications, patents, and printed publications cited herein are incorporated herein by reference in their entireties, except for any definitions, subject matter disclaimers or disavowals, and except to the extent that the incorporated material is inconsistent with the express disclosure herein, in which case the language in this disclosure controls. The various embodiments of the present disclosure may be embodied in other specific forms without departing from the spirit or essential attributes thereof, and it is therefore desired that the various embodiments in the present disclosure be considered in all respects as illustrative and not restrictive. Any headings utilized within the description are for convenience only and have no legal or limiting effect.

What is claimed is:

1. A method for treatment of a chronic pain disorder in a patient, the method comprising administering to the patient a first amount of naltrexone in an immediate-release agent and a second amount of naltrexone in a modified-release agent, wherein the first amount of naltrexone and the second amount of naltrexone combined equal a total amount of naltrexone that does not exceed 5 mg.

2. The method of claim 1, wherein the first amount of naltrexone and the second amount of naltrexone are administered to the patient approximately 1 to 3 hours prior to the patient going to sleep.

3. The method of claim 1, wherein the modified-release agent is a controlled release agent, a sustained release agent or a slow-release agent.

4. The method of claim 1, wherein the second amount of naltrexone is only released to the patient after the first amount of naltrexone has been released to the patient, and wherein the modified-release agent releases the second amount of naltrexone over an extended period of time.

5. The method of claim 1, wherein the modified-release agent releases the second amount of naltrexone over a 30 minute to 2 hour period of time.

6. The method of claim 1, wherein the first amount of naltrexone is approximately 1 mg and wherein the second amount of naltrexone is approximately 1 mg.

7. The method of claim 1, wherein the total amount of naltrexone ranges between approximately 2 mg to 4 mg.

8. The method of claim 1, wherein the first amount of naltrexone and the second amount of naltrexone are administered separately to the patient.

9. The method of claim 1, wherein the first amount of naltrexone and the second amount of naltrexone are administered concurrently to the patient.

10. The method of claim 1, wherein the first amount of naltrexone and the second amount of naltrexone are administered to the patient via a transdermal administration, a transdermal patch, a rectal administration, or orally.

11. The method of claim 1, wherein the first amount of naltrexone and the second amount of naltrexone are administered via a pill ingested by the patient.

12. The method of claim 1, wherein the first amount of naltrexone and the second amount of naltrexone are administered via a pill ingested by the patient, wherein the pill is comprised an inner layer with the second amount of naltrexone and an outer layer with the first amount of naltrexone.

13. The method of claim 1, wherein the first amount of naltrexone and the second amount of naltrexone are administered via a pill ingested by the patient, wherein the pill is comprised an inner layer with the second amount of naltrexone and an outer layer with the first amount of naltrexone, wherein the first amount of naltrexone is approximately 1 mg, and wherein the second amount of naltrexone is approximately 1 mg.

14. A method for treatment of a chronic pain disorder in a patient, the method comprising:
administering daily to the patient a first total amount of naltrexone for an initial period of time, wherein the first total amount of naltrexone is less than 3 mg; and
administering daily to the patient a second total amount of naltrexone after the initial period of time, wherein the second total amount of naltrexone is less than 5 mg, and wherein the second total amount of naltrexone is greater than the first total amount of naltrexone.

15. The method of claim 14, wherein the second total amount of naltrexone is approximately two times greater than the first total amount of naltrexone.

16. The method of claim 14, wherein the first total amount of naltrexone is comprised of a first amount of naltrexone in an immediate-release agent and a second amount of naltrexone in a modified-release agent, and wherein the second total amount of naltrexone is comprised of a third amount of naltrexone in an immediate-release agent and a fourth amount of naltrexone in a modified-release agent.

17. The method of claim 16, wherein the first amount of naltrexone is approximately 1 mg, wherein the second amount of naltrexone is approximately 1 mg, wherein the third amount of naltrexone is approximately 2 mg, and wherein the fourth amount of naltrexone is approximately 2 mg.

18. The method of claim 17, wherein the first amount of naltrexone and the second amount of naltrexone are administered via a first pill ingested by the patient, wherein the first pill is comprised an inner layer with the second amount of naltrexone and an outer layer with the first amount of naltrexone.

19. A method for treatment of a chronic pain disorder in a patient, the method comprising:

administering daily to the patient a first pill having a first total amount of naltrexone for an initial period, wherein the first total amount of naltrexone is comprised of a first amount of naltrexone in an immediate-release agent and a second amount of naltrexone in a modified-release agent, wherein the first amount of naltrexone is approximately 1 mg, wherein the second amount of naltrexone is approximately 1 mg, wherein the first amount of naltrexone and the second amount of naltrexone are administered via a first pill ingested by the patient, and wherein the first pill is comprised an inner layer with the second amount of naltrexone and an outer layer with the first amount of naltrexone; and administering daily to the patient a second pill having a second total amount of naltrexone after the initial period of time, wherein the second total amount of naltrexone is comprised of a third amount of naltrexone in an immediate-release agent and a fourth amount of naltrexone in a modified-release agent, wherein the third amount of naltrexone is approximately 2 mg, wherein the fourth amount of naltrexone is approximately 2 mg, wherein the third amount of naltrexone and the fourth amount of naltrexone are administered via at least one second pill ingested by the patient, and wherein the at least one second pill is comprised an inner layer with the fourth amount of naltrexone and an outer layer with the third amount of naltrexone.

20. The method of claim 19, wherein the initial period is comprised of approximately four weeks.

* * * * *